United States Patent
Chitwood

Patent Number: 5,709,649
Date of Patent: Jan. 20, 1998

[54] NECK CURVATURE ALIGNMENT DEVICE

[75] Inventor: Ralph M. Chitwood, Kalispell, Mont.

[73] Assignee: Glacier Cross, Inc., Kalispell, Mont.

[21] Appl. No.: 582,676

[22] Filed: Jan. 4, 1996

Related U.S. Application Data

[63] Continuation-in-part of Ser. No. 516,007, Aug. 16, 1995, which is a continuation-in-part of Ser. No. 327,021, Oct. 21, 1994, Pat. No. 5,569,175, which is a continuation-in-part of Ser. No. 120,602, Sep. 13, 1993, Pat. No. 5,441,479.

[51] Int. Cl.$^6$ .................................................. A61H 1/02
[52] U.S. Cl. ............................... 602/32; 602/36; 128/845; 606/237
[58] Field of Search ........................... 602/32, 33, 35, 602/36; 601/23, 39, 148, 149, 150; 606/234, 240; 5/622, 636, 637, 640, 644; 128/845, 840, DIG. 20

[56] References Cited

U.S. PATENT DOCUMENTS

| | | | |
|---|---|---|---|
| 2,831,482 | 4/1958 | Cobb | 602/36 |
| 4,285,081 | 8/1981 | Price | 5/637 |
| 4,508,109 | 4/1985 | Saunders . | |
| 4,528,705 | 7/1985 | Grenawalt | 5/636 |
| 4,616,814 | 10/1986 | Harwood-Nash et al. | 5/622 |
| 4,617,691 | 10/1986 | Monti et al. . | |
| 4,625,348 | 12/1986 | Renggli et al. | 5/622 |
| 4,702,235 | 10/1987 | Hong | 602/13 |
| 4,736,736 | 4/1988 | Moers et al. | 602/32 |
| 4,771,493 | 9/1988 | Park . | |
| 4,784,122 | 11/1988 | Graham | 602/35 |
| 4,805,603 | 2/1989 | Cumberland . | |
| 4,823,776 | 4/1989 | Foster et al. | 601/148 |
| 4,832,007 | 5/1989 | Davis, Jr. et al. . | |
| 5,067,483 | 11/1991 | Freed . | |
| 5,070,865 | 12/1991 | Iams | 606/240 |
| 5,147,287 | 9/1992 | Jewell et al. | 602/32 |
| 5,243,726 | 9/1993 | Bisbee | 5/610 |
| 5,382,226 | 1/1995 | Graham . | |
| 5,409,452 | 4/1995 | Aversano . | |
| 5,416,939 | 5/1995 | Maalouli | 5/610 |
| 5,528,783 | 6/1996 | Kunz et al. | 5/644 |
| 5,577,503 | 11/1996 | Bonutti | 5/622 |

FOREIGN PATENT DOCUMENTS

| | | | |
|---|---|---|---|
| 2388548 | 12/1978 | France | 602/32 |

*Primary Examiner*—Jeanne M. Clark
*Attorney, Agent, or Firm*—Thomas R. Vigil

[57] ABSTRACT

The neck curvature alignment device comprises: a framework including a base portion adapted to be supported on a generally planar surface and having an upper surface and a pivot portion having an outer surface and being pivotally connected to the base portion; a moving mechanism situated between the base portion and the pivot portion for moving the pivot portion away from the base portion; a device for actuating the moving mechanism; a head and neck receiving device mounted on the upper surface of the base portion and having structure for engaging and bearing against the occipital bone of a patient's head, whereby operation of the moving mechanism will cause the pivot portion to move away from the base portion to cause the head and neck receiving portion to act in an arcuate direction against a patient's neck and head.

19 Claims, 5 Drawing Sheets

NECK CURVATURE ALIGNMENT DEVICE

CROSS-REFERENCE TO RELATED APPLICATIONS

This application is a continuation-in-part of U.S. application Ser. No. 08/516,007 filed on Aug. 16, 1995, which is a continuation-in-part of U.S. application Ser. No. 08/327,021 filed on Oct. 21, 1994, now U.S. Pat. No. 5,569,175, issued Oct. 29, 1996, which is a continuation-in-part of U.S. application Ser. No. 08/120,602 filed on Sep. 13, 1993, now U.S. Pat. No. 5,441,479, issued Aug. 15, 1995.

BACKGROUND OF THE INVENTION

1. Field of the Invention

The present invention relates to a neck curvature alignment device which can be used by a user of the neck curvature alignment device, a patient or by a trained technician. The neck curvature alignment device includes a head and neck receiving device which has head and neck receiving surfaces including an occipital bone lift surface and a ridge or shoulder adjacent the lift surface of the head and neck receiving device for engaging the occipital bone of the user's/patient's head.

2. Description of the Related Art Including Information Disclosed under 37 CFR §§1.97-1.99

Heretofore various types of neck treatment devices and cervical traction devices have been proposed.

Examples of previously proposed analogous and nonanalogous devices are disclosed in the following U.S. patents:

| U.S. Pat. No. | Patentee |
|---|---|
| 4,508,109 | Saunders |
| 4,617,691 | Monti et al. |
| 4,771,493 | Park |
| 4,805,603 | Cumberland |
| 4,832,007 | Davis, Jr. et al. |
| 5,067 483 | Freed |
| 5,382,226 | Graham |
| 5,409,452 | Aversano |

The Cumberland U.S. Pat. No. 4,805,603 discloses an inflatable cervical traction pillow comprising a head/neck/shoulder support unit having a vertical slot in the region corresponding to the cervical area and a bellows located in the area of the slot. The Cumberland inflatable cervical traction pillow is designed for stretching of the cervical area of the neck.

The Davis, Jr. et al. U.S. Pat. No. 4,832,007 discloses a traction pillow made of resilient material having a generally rotatable portion (cervical roll) for supporting the cervical region of a user. A user's neck is received across the pillow cervical roll and the user's head is received on the pillow. Then, rotation of the cervical roll in conjunction with collapse of angled chambers within the resilient pillow establish traction in the cervical region of the user. Once the internal chambers inside the pillow are fully collapsed, the pillow provides a generally continuous support medium for resilient support of the user's neck and head, while maintaining a degree of cervical region traction with natural cervical curvature achieved as a result of the curved support of the user's cervical region by the cervical roll of the pillow.

The Freed U.S. Pat. No. 5,067,483 discloses a cervical traction device which includes a head support section for the neck and head of the patient having an occipital pad which has a reversed angled surface which causes increased cervical flexion when the device is in use.

The angle of the tractive force is adjustable to an angle of a few degrees. Further, the traction applied with the device is controlled by use of an air cylinder directly affixed to the head support device.

The Graham U.S. Pat. No. 5,382,226 discloses an inflatable cervical traction and exercising device that is adapted to be secured about the head and neck of a user for imparting a desired lordotic shape into the cervical region of the spine and for manipulating the spine and surrounding tissue to promote fluid and cellular exchange in and around the intervertebral discs. The device includes a frame, an upstanding neck support carried by the frame, an inflatable elongated bladder carried by the neck support, restraining straps for securing the device to the user's head so that the inflatable bladder is disposed below and adjacent the user's neck, and a bulb type air pump for selectively inflating and deflating the bladder to force the cervical spine upwardly thereby to cause it to move forwardly and apply angular traction to the spine.

As will be described in greater detail hereinafter, the neck curvature alignment device of the present invention differs from the previously proposed neck treatment devices by providing a pivot axis located above a person's head whereby a head and neck receiving device of the alignment neck curvature alignment device can be moved through an arc, e.g., between 0° to as high as 45° to the horizontal about the pivot axis thereby to reset the cervical curve back to a person's/user's neck while at the same time exerting traction to the spine.

SUMMARY OF THE INVENTION

According to the present invention there is provided a neck curvature alignment device comprising:

- a framework including a base portion adapted to be supported on a generally planar surface and having an upper surface and a pivot portion having an outer surface and being pivotally connected to the base portion;
- a moving mechanism situated between the base portion and the pivot portion for moving the pivot portion away from the base portion;
- a device for actuating the moving mechanism;
- a head and neck receiving device mounted on the upper surface of the base portion and having structure for engaging and bearing against the occipital bone of a patient's head, whereby operation of the moving mechanism will cause the pivot portion to move away from the base portion to cause the head and neck receiving portion to act in an arcuate direction against a patient's neck and head.

DESCRIPTION OF THE PREFERRED EMBODIMENT(S)

Figure 1:
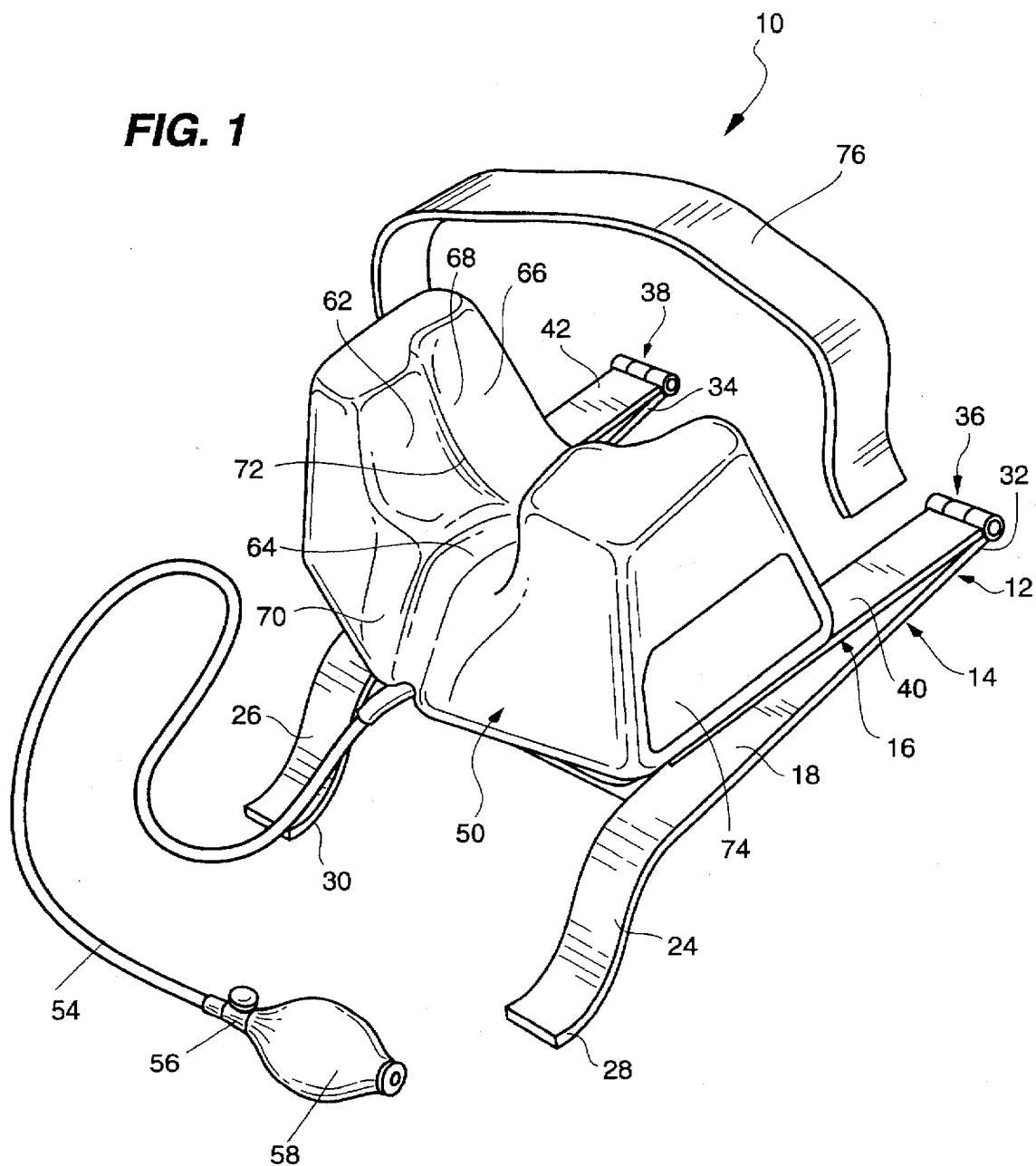
FIG. 1 is a partially exploded perspective view of a neck curvature alignment device constructed according to the teaching of the present invention.
Figure 2:
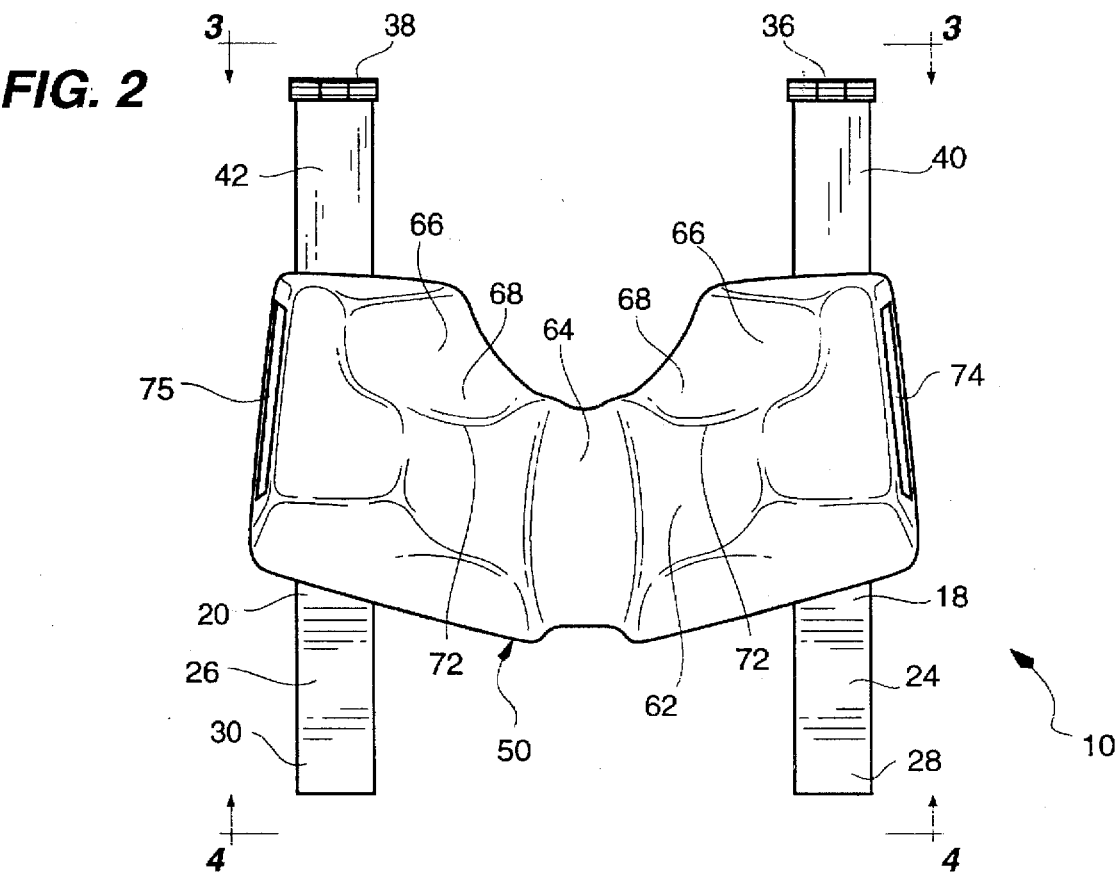
FIG. 2 is a top plan view of the neck curvature alignment device shown in FIG. 1.
Figure 3:
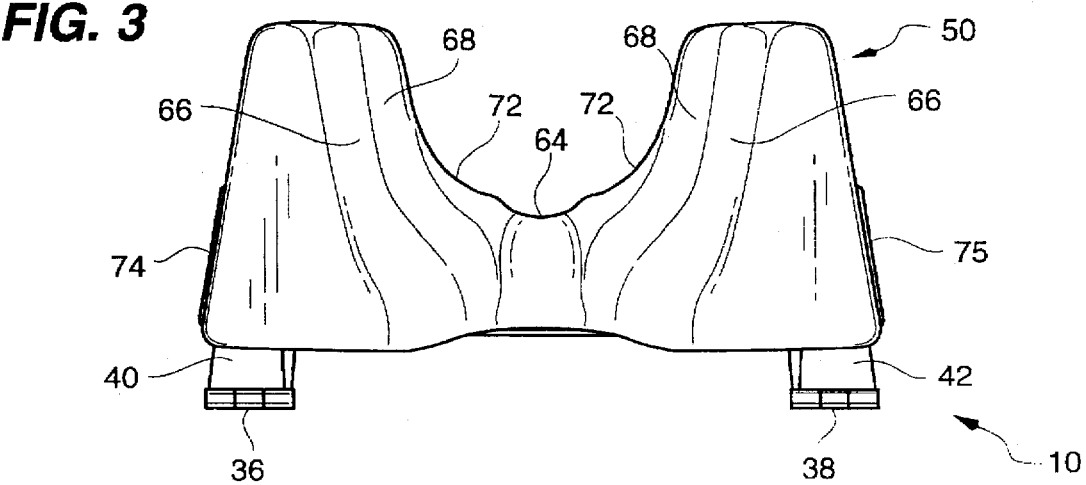
FIG. 3 is one elevational end view of the neck curvature alignment device shown in FIG. 2 and is taken along line 3—3 of FIG. 2.
Figure 4:
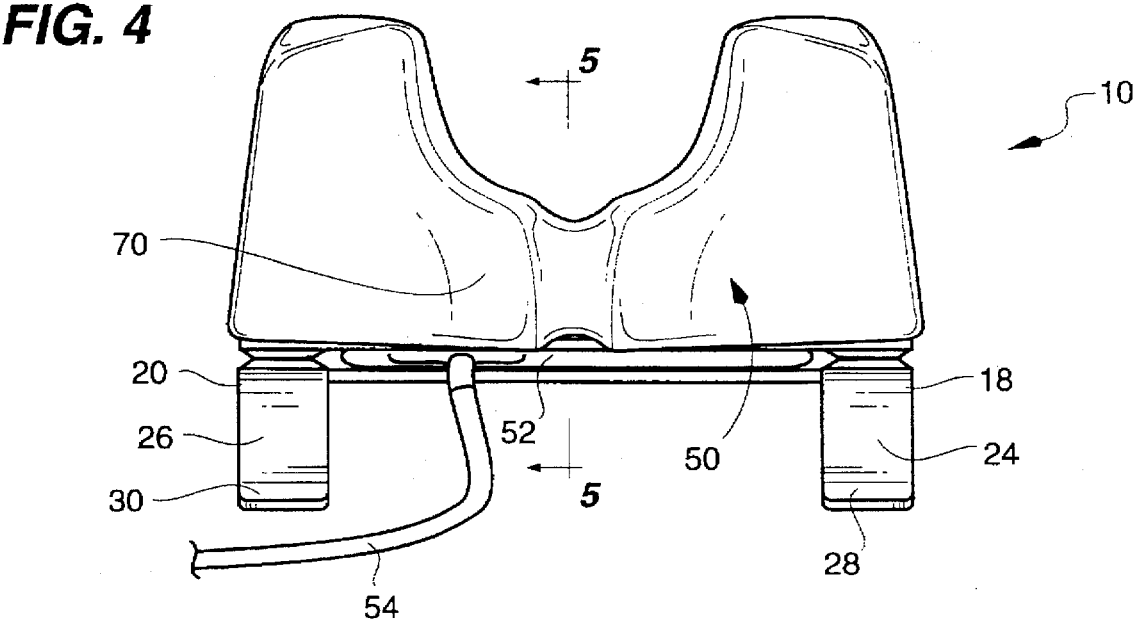
FIG. 4 is an opposite elevational end view of the neck curvature alignment device shown in FIG. 2 and is taken along line 4—4 of FIG. 2.
Figure 6:
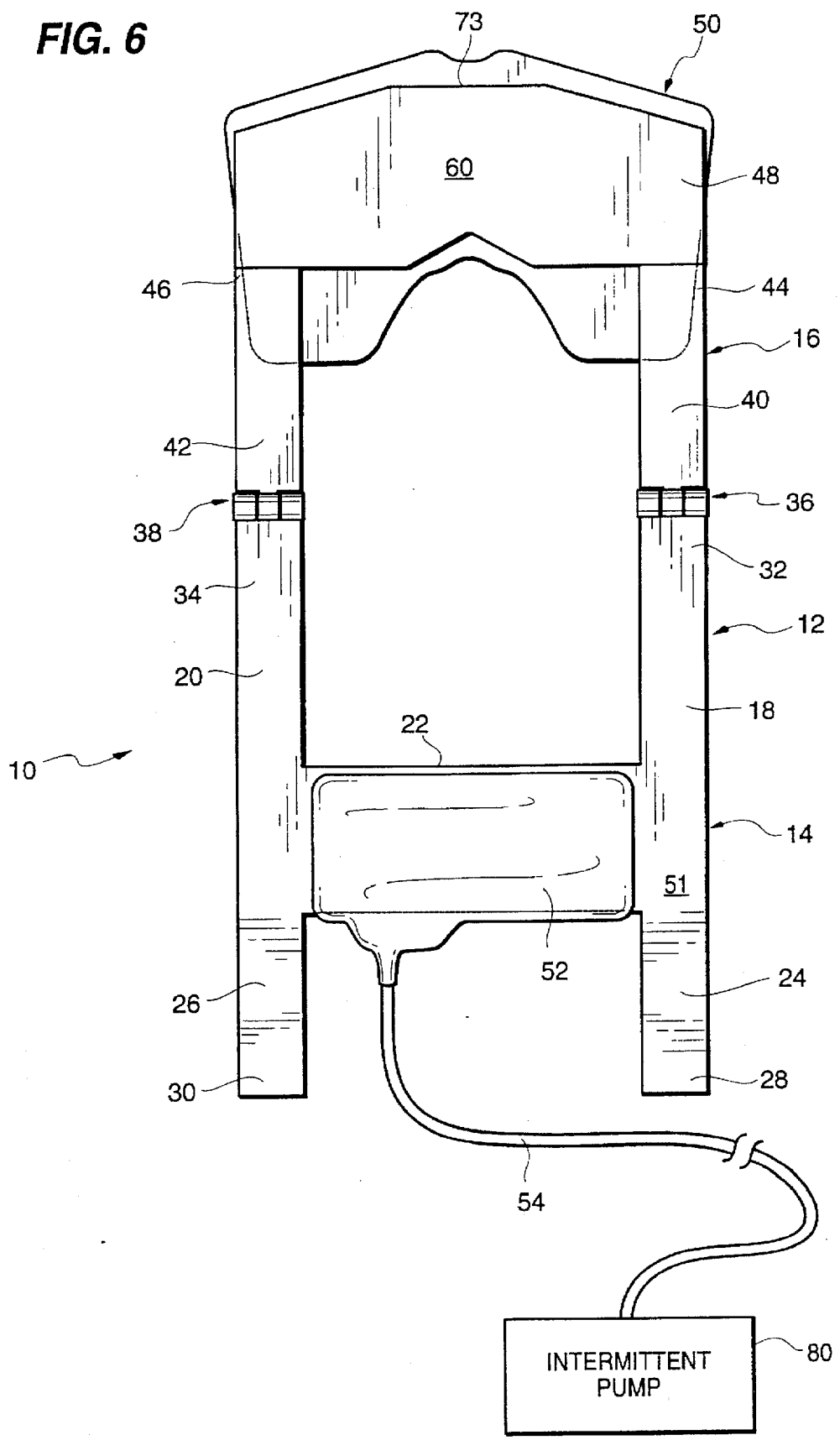
FIG. 6 is a folded out plan view of the neck curvature alignment device shown in FIG. 1 and shows a bellows on a framework which will be located beneath a head and neck receiving device of the neck curvature alignment device when the neck curvature alignment device is folded to the position shown in FIG. 1.
Figure 7:
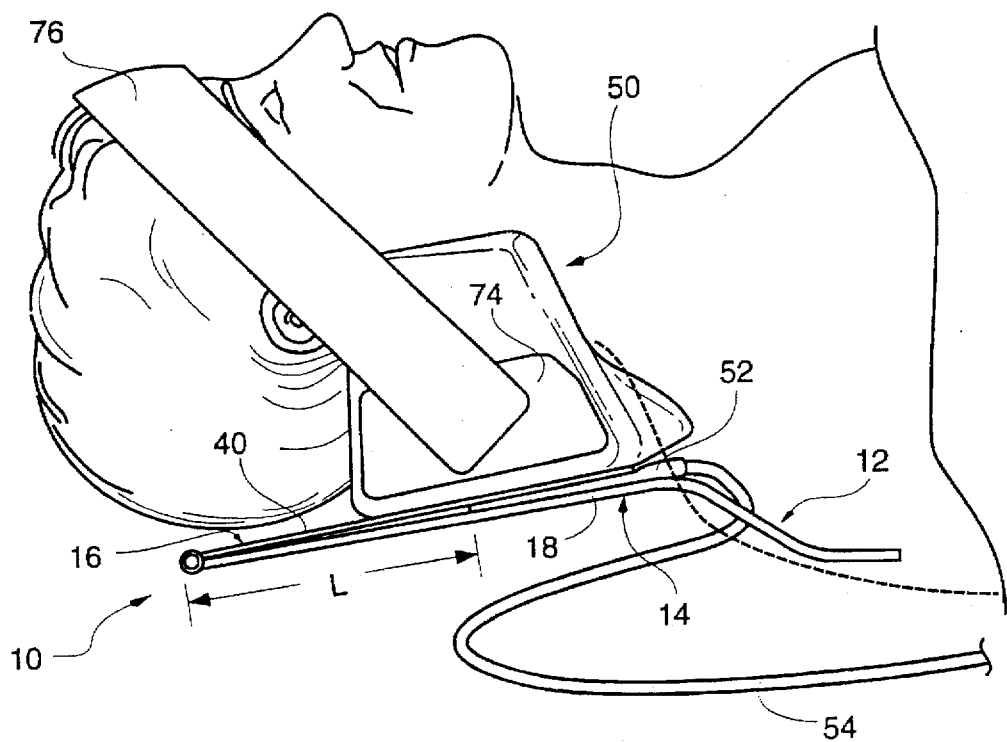
FIG. 7 is a side elevational view of the neck curvature alignment device shown in FIG. 1 and shows a patient's head received in the head and neck receiving device without inflation of the bellows.
Figure 8:
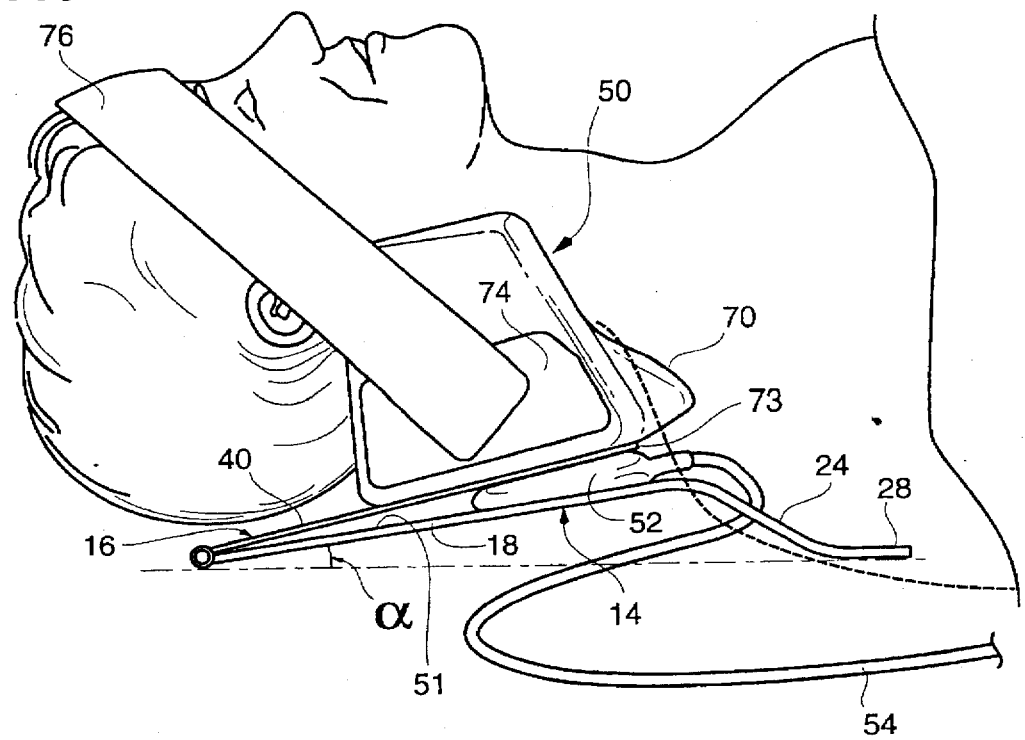
FIG. 8 is a side elevational view of the neck curvature alignment device, similar to the view shown in FIG. 7, and shows the bellows at least partially inflated to raise the head and neck receiving device for aligning the curvature of the neck of the patient.

Referring now to FIG. 1 is greater detail, there is illustrated therein, a neck curvature alignment device 10 constructed according to the teachings of the present invention. The neck curvature alignment device 10 includes a generally rectangular framework 12 including a base portion 14 and a pivot portion 16. The base portion 14 has a generally H-shape including a first leg 18 and a second leg 20 interconnected by a transverse middle leg 22, as best shown in FIG. 6. Each leg 18 and 20 has a bent end portion 24 and 26, which extend downwardly and then outwardly so as to form a slight S or Z-shape, as best shown in FIGS. 1, 7 or 8. The outer ends 28 and 30 of the legs 18 and 20 define rests, feet or stops 28 and 30 for resting on a planar surface.

At the other end 32, 34 of each leg 18 and 20 is a hinge assembly 36 or 38 for connecting to respective legs 40 and 42 of the pivot portion 16. As shown in FIG. 6, the pivot portion 16 has a generally C-shape, being interconnected at outer ends 44 and 46 (FIG. 6) of the legs 40 and 42 by a support plate 48 having an outer surface 49 (FIG. 5) on which is received and mounted a head and neck receiving device 50 constructed according to the teachings of the present invention. The head and neck receiving device 50 can be of the type disclosed in applicant's earlier patent applications referred to above, and in particular in U.S. patent application Ser. No. 08/516,007 filed Aug. 16, 1995 entitled: GRAVITY TRACTION DEVICE, the disclosure of which is incorporated herein by reference.

As best shown in FIG. 6, on an upper side 51 of the transverse leg 22 of the base portion 14 is mounted a mechanism, namely an inflatable member or bellows 52, which is made of an elastomeric material having a tubing 54 extending therefrom, first to a relief valve 56 and then to a bulb type air pump 58, for moving the pivot portion 16. The tubing 54 is of sufficient length to enable a user/patient to comfortably grasp the bulb pump 58 in his hand to pump up the bellows 52 which then acts against an inner side 60 (FIG. 6) of the support plate 48 of the pivot portion 16 to move the head and neck receiving device 50 arcuately, upwardly above the horizontal and above the user's/patient's head.

It will be understood that the head and neck receiving device 50 is secured, such as by an adhesive or by hook and loop type fastening structure of the type sold under the trademark VELCRO®, to the outer surface 49 of the transversely extending support plate 48 of the pivot portion 16.

Important features of the head and neck receiving device 50 are described in the parent application and are generally described below.

With particular reference to FIGS. 1–5, the head and neck receiving device 50 has a generally arcuate or semi-cylindrical U-shaped surface 62 having a cervical curve receiving portion 64 at the center of the head and neck receiving device 50 sized to fit and support the cervical curve of a patient's neck and has a head and neck receiving surface 66 including a lift portion 68 that curves downwardly and inwardly for mating with the cervical curve receiving portion 64.

The U-shaped surface 62 also extends toward an inner or lower end 70 of the head and neck receiving device 50 a distance of approximately ¾ of an inch to one inch and forms a ridge or shoulder 72 (FIGS. 1, 3 and 5) on opposite sides of the curved U-shaped surface 62 but not at the center of the U-shaped surface 62.

Part way up from the cervical curve receiving portion 64, on either side of the U-shaped surface 62, the ridge or shoulder 72 is pronounced and is located at the junction between the U-shaped surface 62 and the head and neck receiving surface 66. The ridge or shoulder 72 at this location is adapted to bear against the occipital bone and defines in the adjacent head and neck receiving surface 66 the occipital/cervical lift or pressure applying surface 68 just outwardly of the ridge or shoulder 72 in the head and neck receiving surface 66.

This ridge or shoulder 72 and the adjacent pressure or lift surface 68 of the head and neck receiving surface 66 enables the head and neck receiving device 50 to apply pressure at the region of the occipital bone of a patient on each side of the neck. It is believed that this pressure on the occipital bone applied with the neck curvature alignment device 10 of the present invention can serve to reset a cervical curve into the user's/patient's neck.

According to the teachings of the present invention, pumping of the bellows 52 by the patient will cause the pivot portion 16 to pivot about the two hinges 36 and 38 upwardly toward the patient's neck and to place an arcuately directed pressure, by the occipital lift surface 68, against a user's/patient's head and neck to reset the user's neck curvature. This is best shown in FIG. 8.

The legs 18 and 20 of the base portion 14 at the hinges 36 and 38 can be at an angle α to the horizontal of between 2° and 6° just to provide a slight inclined angle for the start of the pumping of the bellows 52. Then, as the bellows 52 is pumped, the pivot portion 16 is moved in angle relative to the horizontal of between 2° and 45°, depending upon how much pressure a patient can withstand.

An important feature of applicant's neck curvature alignment device is that pressure is always controlled by the patient pumping the bulb pump 58, and the patient can pump as much air as is needed to correct his/her cervical curve alignment and to place traction on his/her spine.

Figure 5:
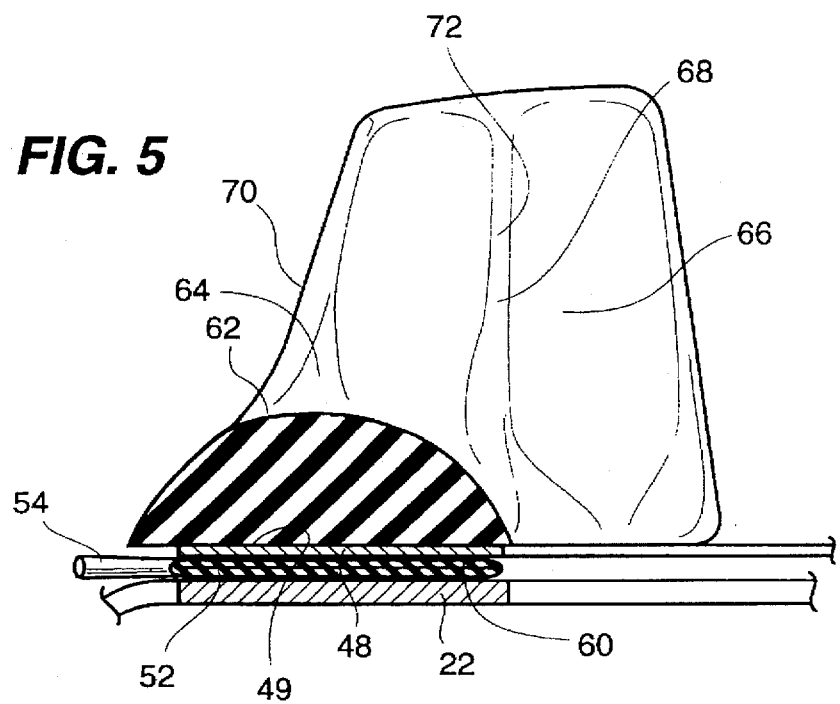
FIG. 5 is a sectional view of the neck curvature alignment device shown in FIG. 4 and is taken along line 5—5 of FIG. 4.

Although it is not known with absolute certainty, it is believed that the radius of the arcuate force being placed on the head should be a distance L, as shown in FIG. 5, of between 3 inches and 10 inches, and preferably about 5 to 6 inches. The point where the force is applied is approximately four to five inches from a top edge 73 of the transverse support plate 48 of the pivot portion 16 and the legs 40 and 42 each have a length of between 9 and 11 inches, the legs 18 and 20 being longer, i.e., generally between 12 and 18 inches.

Referring again to FIGS. 1, 2, 7 and 8, the head and neck receiving device 50 has on either side thereof, a hook or loop type fastening structure 74, 75 of the type sold under the trademark VELCRO® and a head strap 76 which is received over the patient's head to be secured to the fastening structure 73, 74.

The strap 76 holds the patient properly and securely in the head and neck receiving device 50 for the best benefit of the occipital lift and immobilizes the patient's head for accuracy in treatment.

From the foregoing description, it will be apparent that the neck curvature alignment device 10 of the present invention has a number of advantages, some of which have been described above and others of which are inherent in the invention.

Also from the foregoing description, it will apparent that modifications can be made to the neck curvature alignment device 10 of the present invention without departing from the teachings of the invention. For example, an intermittently operated electric motor driven pump can be used in place of the bulb type air pump 58 to provide slowly pulsating pressure on the occipital bone area of a user's/ patient's head.

Accordingly, the scope of the invention is only to be limited as necessitated by the accompanying claims.

I claim:

1. A neck curvature alignment device for use by a person and comprising:

a framework including a base portion which is supported on a generally planar surface and which has an upper surface and a pivot portion which has an outer surface and which is pivotally connected at one end by a pivot connection to said base portion;

a moving mechanism situated between said base portion and said pivot portion for moving said pivot portion away from said base portion;

means for actuating said moving mechanism;

a head and neck receiving device having an outer end and an inner end, a neck receiving portion and a head receiving portion between said neck receiving portion and said outer end and being mounted on said outer surface of said pivot portion, said neck receiving portion having a top and a U-shaped surface extending dowardly for receiving a persons neck and said head receiving portion also having a top, a U-shaped surface extending dowardly for receiving the back of a persons head, a ridge separating said head receiving portion from said neck receiving portion and support structure in the form of an adjacent contoured lift surface for engaging and bearing against the occipital bone of a patient's head with an arcuate force, said pivot connection being located outwardly of said outer end and of said head receiving portion, whereby operation of said moving mechanism will cause said pivot portion to move away from said base portion to cause said head and neck receiving portion to act in an arcuate direction upwardly toward a patients forehead and against the patient's neck and head; and, the radius of the arcuate force from said pivot connection to the area where said support structure acts against the person's head being between three inches and ten inches.

2. The neck curvature alignment device of claim 1 further comprising a head strap connected to said head and neck device and about a user's or patient's head.

3. The neck curvature alignment device of claim 1 wherein said moving mechanism includes a bellows which is mounted to said upper surface of a transverse leg of said base portion and is generally rectangular in shape.

4. The neck curvature alignment device of claim 3 wherein said bellows is made of an elastomeric material and is of such a size that it can move said pivot portion upwardly and outwardly up to 45° away from said base portion.

5. The neck curvature alignment device of claim 1 wherein said moving mechanism for moving said pivot portion away from said base portion includes a bellows fixed to an upper surface of said base portion and said actuating means includes a pump for pumping a gas into said bellows.

6. The neck curvature alignment device of claim 5 wherein said pump is a bulb type pump connected by a tubing to said bellows.

7. The neck curvature alignment device of claim 6 wherein said tubing has a relief valve mounted therein.

8. A neck curvature alignment device for use by a person and comprising:

a framework including a base portion which is supported on a generally planar surface and which has an upper surface and a pivot portion which has an outer surface and which is pivotally connected at one end by a pivot connection to said base portion;

a moving mechanism situated between said base portion and said pivot portion for moving said pivot portion away from said base portion;

means for actuating said moving mechanism;

a head and neck receiving device having an outer end and an inner end, a neck receiving portion and a head receiving portion between said neck receiving portion and said outer end and being mounted on said outer surface of said pivot portion, said head receiving portion having support structure for engaging and bearing against the occipital bone of a patient's head with an arcuate force, said pivot connection being located outwardly of said outer end and of said head receiving portion, whereby operation of said moving mechanism will cause said pivot portion to move away from said base portion to cause said head and neck receiving portion to act in an arcuate direction upwardly toward a patients forehead and against the patient's neck and head;

the radius of the arcuate force from said pivot connection to the area where said support structure acts against the person's head being between three inches and ten inches; and, said base portion including first and second legs interconnected by a transverse cross-leg and a hinge defining said pivot connection at one end of each of said first and second legs.

9. The neck curvature alignment device of claim 8 wherein the angle between a supporting surface supporting said legs of said base portion and a plane containing said legs of said base portion is between 2° and 6°.

10. The neck curvature alignment device of claim 8 wherein said pivot portion comprises first and second legs each pivotally connected, respectively, to said first and second legs of said base portion.

11. The neck curvature alignment device of claim 10 wherein said pivot portion has, at an outer end opposite said pivot connection at said one end, a cross-plate so as to form said pivot portion with a generally C-shape and said head and neck receiving device is mounted to an outer surface of said cross-plate.

12. The neck curvature alignment device of claim 3 wherein said actuating means includes an intermittently operated pump.

13. A neck curvature alignment device comprising:

a framework including a base portion which is supported on a generally planar surface and which has an upper surface and a pivot portion which has an outer surface and which is pivotally connected to said base portion;

said base portion including first and second legs interconnected by a transverse cross-leg;

a hinge at one end of each of said first and second legs a moving mechanism situated between said base portion and said pivot portion for moving said pivot portion away from said base portion;

means for actuating said moving mechanism;

a head and neck receiving device mounted on said outer surface of said pivot portion and having support structure for engaging and bearing against the occipital bone of a patient's head, whereby operation of said moving mechanism will cause said pivot portion to move away from said base portion to cause said head and neck receiving portion to act in an arcuate direction against a patient's neck and head; and, the other end of each of said first and second legs having a slightly S or Z-shape to provide an offset end portion which rests on the generally planar surface.

14. A neck curvature alignment device comprising:

a framework including a base portion which is supported on a generally planar surface and which has an upper surface and a pivot portion which has an outer surface and which is pivotally connected to said base portion;

said base portion including first and second legs interconnected by a transverse cross-leg;

a hinge at one end of each of said first and second legs;

said pivot portion comprising first and second legs each pivotally connected, respectively, to said first and second legs of said base portion a moving mechanism situated between said base portion and said pivot portion for moving said pivot portion away from said base portion;

means for actuating said moving mechanism;

a head and neck receiving device mounted on said outer surface of said plate portion and having support structure for engaging and bearing against the occipital bone of a patient's head, whereby operation of said moving mechanism will cause said pivot portion to move away from said base portion to cause said head and neck receiving portion to act in an arcuate direction against a patient's neck and head;

said pivot portion including a transversely extending support plate at its outer end; and, the distance from said pivot connection between said first and second legs of said pivot portion and said first and second legs of said base portion to the area of said support structure on said head and neck receiving device which engages against the occipital bone of the user/patient being between 3 inches and 10 inches.

15. The neck curvature alignment device of claim 12 wherein the distance from said pivot connection between said first and second legs of said pivot portion and said first and second legs of said base portion to the area of said support structure on said head and neck receiving device which engages against the occipital bone of the user/patient is between 5 inches and 6 inches.

16. A neck curvature alignment device comprising:

a framework including a base portion which is supported on a generally planar surface and which has an upper surface and a pivot portion which has an outer surface and which is pivotally connected to said base portion;

said base portion including first and second legs interconnected by a transverse cross-leg;

a hinge at one end of each of said first and second legs;

said pivot portion comprising first and second legs each pivotally connected, respectively, to said first and second legs of said base portion a moving mechanism situated between said base portion and said pivot portion for moving said pivot portion away from said base portion;

means for actuating said moving mechanism;

a head and neck receiving device mounted on said outer surface of said pivot portion and having support structure for engaging and bearing against the occipital bone of a patient's head, whereby operation of said moving mechanism will cause said pivot portion to move away from said base portion to cause said head and neck receiving portion to act in an arcuate direction against a patient's neck and head; and, the length of each of said first and second legs of said pivot portion being generally between 9 inches and 11 inches.

17. A neck curvature alignment device comprising:

a framework including a base portion which is to be supported on a generally planar surface and which has an upper surface and a pivot portion which has an outer surface and which is pivotally connected to said base portion;

said base portion including first and second legs interconnected by a transverse cross-leg;

a hinge at one end of each of said first and second legs a moving mechanism situated between said base portion and said pivot portion for moving said pivot portion away from said base portion;

means for actuating said moving mechanism;

a head and neck receiving device mounted on said outer surface of said pivot portion and having support structure for engaging and bearing against the occipital bone of a patient's head, whereby operation of said moving mechanism will cause said pivot portion to move away from said base portion to cause said head and neck receiving portion to act in an arcuate direction against a patient's neck and head; and, the angle between the generally planar supporting surface supporting said legs of said base portion and a plane containing said legs of said base portion is between 2° and 6°.

18. A neck curvature alignment device for use by a person and comprising:

a framework including a base portion which is supported on a generally planar surface and which has an upper surface and a pivot portion which has an outer surface and which is pivotally connected at one end by a pivot connection to said base portion, said framework being capable of being positioned beneath a person's head for pivotal movement in an arcuate direction from the person's neck toward the person's forehead;

a moving mechanism situated between said base portion and said pivot portion for moving said pivot portion away from said base portion and, when positioned beneath the persons head, in a direction toward the person's forehead;

means for actuating said moving mechanism;

a head and neck receiving device having an outer end and an inner end, a neck receiving portion and a head receiving portion between said neck receiving portion and said outer end and being mounted on said outer surface of said pivot portion, said neck receiving portion having a top and a U-shaped surface extending downwardly from said top for receiving a persons neck and said head receiving portion having a top, a U-shaped surface extending downwardly for receiving the back of a persons head, a ridge separating said head receiving portion from said neck receiving portion and support structure in the form of an adjacent contoured lift surface for engaging and bearing against the occipital bone of a person's head, and said pivot connection being located outwardly of said outer end and of said head receiving portion, whereby operation of said moving mechanism will cause said pivot portion to move away from said base portion to cause said head and neck receiving device to act in an arcuate direction against a person's neck and head received therein, the arcuate direction being upwardly from the back of the person's neck and in an arc toward the person's forehead; and, the radius of the arcuate force from said pivot connection to the area where said lift surface acts against the person's head being between three inches and ten inches.

19. A neck curvature alignment device for use by a person and comprising:

a framework including a base portion which is supported on a generally planar surface and which has an upper surface and a pivot portion which has an outer surface and which is pivotally connected at one end by a pivot connection to said base portion, said framework being capable of being positioned beneath a person's head for pivotal movement in an arcuate direction from the back of the person's neck upwardly toward the person's forehead;

a moving mechanism situated between said base portion and said pivot portion for moving said pivot portion away from said base portion and, when positioned beneath the persons head, in a direction toward the person's forehead;

means for actuating said moving mechanism; and, a head and neck receiving device having an outer end and an inner end, a neck receiving portion and a head receiving portion between said neck receiving portion and said outer end and being mounted on said outer surface of said pivot portion and said neck receiving portion having a top and a U-shaped surface extending downwardly from said top for receiving a persons neck and said head receiving portion having a top, a U-shaped surface extending downwardly for receiving the back of a persons head, a ridge separating said head receiving portion from said neck receiving portion and support structure in the form of an adjacent contoured lift surface for engaging and bearing against the occipital bone of a person's head, and said pivot connection being located outwardly of said outer end and of said head receiving portion, whereby operation of said moving mechanism will cause said pivot portion to move away from said base portion to cause said head and neck receiving device to act in an arcuate direction against a person's neck and head, the arcuate direction being upwardly from the back of the person's neck and in an arc toward the person's forehead so as to push the person's head upwardly and horizontally away from the persons body and, at the same time, exert a stretching force on the person's neck.

* * * * *

UNITED STATES PATENT AND TRADEMARK OFFICE
CERTIFICATE OF CORRECTION

PATENT NO. : 5,709,649

DATED : January 20, 1998

INVENTOR(S) : Ralph M. Chitwood

Page 1 of 2

It is certified that error appears in the above-identified patent and that said Letters Patent is hereby corrected as shown below:

On the title page, Item [63], delete the data and insert, ------Continuation-in-part of Ser. No. 327,021, Oct. 21, 1994, Pat. No. 5,569,175, which is a continuation-in-part of Ser. No. 303,691, Sept. 9, 1994, Pat. No. 5,454,781, which is a continuation-in-part of Ser. No. 120,602, Sept. 13, 1993, Pat. No. 5,441,479.------, which includes editing the change in accordance with the present style for printing.

Column 1, delete lines 5-11 and insert

-- This application is a continuation-in-part of U.S. Application Serial No. 08/327,021, filed on October 21, 1994, now U.S. Patent No. 5,569,175, which is a continuation-in-part of U.S. Application Serial No. 08/303,691, filed on September 9, 1994, now U.S. Patent No. 5,454,781, issued October 2, 1995, which is a continuation-in-part of U.S. Application Serial No. 08/120,602, filed on September 13, 1993, now U.S. Patent No. 5,441,479, issued August 15, 1995. --

UNITED STATES PATENT AND TRADEMARK OFFICE
CERTIFICATE OF CORRECTION

PATENT NO.   : 5,709,649
DATED        : January 20, 1998
INVENTOR(S)  : Ralph M. Chitwood It is certified that error appears in the above-identified patent and that said Letters Patent is hereby corrected as shown below:

Column 5, line 13, after "pump" insert -- 80 (FIG. 6) --.

Column 5, line 38, change "dowardly" to -- downwardly --.

Column 5, line 40, change "dowardly" to -- downwardly --.

Signed and Sealed this

Eighth Day of December, 1998

*Attest:*

*Attesting Officer*

BRUCE LEHMAN

*Commissioner of Patents and Trademarks*